United States Patent [19]

Sauer

[11] Patent Number: 4,892,098
[45] Date of Patent: Jan. 9, 1990

[54] TUBULAR TISSUE WELDING DEVICE WITHOUT MOVING PARTS

[76] Inventor: Jude S. Sauer, 62½ Lattimore Rd., Rochester, N.Y. 14620

[21] Appl. No.: 160,158

[22] Filed: Feb. 25, 1988

Related U.S. Application Data

[60] Continuation-in-part of Ser. No. 919,954, Oct. 17, 1986, abandoned, which is a division of Ser. No. 748,972, Jun. 26, 1985, Pat. No. 4,633,870.

[51] Int. Cl.⁴ .................. A61B 17/04; A61B 17/36; B23K 9/00
[52] U.S. Cl. .................................. 606/18; 219/121.63
[58] Field of Search ........... 128/334 R, 303.1, 303.13, 128/303.12; 219/121 LU, 121 L

[56] References Cited

U.S. PATENT DOCUMENTS

| | | | |
|---|---|---|---|
| 3,786,817 | 1/1974 | Palma | 128/334 R |
| 3,960,151 | 6/1976 | Kuhn | 128/334 R |
| 4,306,561 | 12/1981 | de Medinaceli | 128/303.13 |
| 4,625,724 | 12/1986 | Suzuki et al. | 128/303.1 |
| 4,633,870 | 1/1987 | Sauer | 128/303.1 |
| 4,660,925 | 4/1987 | McCaughan | 128/303.1 |

FOREIGN PATENT DOCUMENTS

| | | | |
|---|---|---|---|
| 0618115 | 8/1978 | U.S.S.R. | 128/303.1 |
| 0618116 | 8/1978 | U.S.S.R. | 128/303.1 |
| 1091933 | 5/1984 | U.S.S.R. | 128/303.1 |

OTHER PUBLICATIONS

"Hot Tip": Another Method of Laser Vascular Recanulization, Alan R. Liss, Inc. 1985.
Mercer et al: Sutureless Bowel Anastomosis Using Nd:YAG Laser, Lasers Surg. Med 7:503–506, 1987.
Clark, A. J.: Laser Welding May Be Alternatives to Suturing Tissues. Research Resources Reporter, vol. 12, No. 5, 1–5, May 1988.

Primary Examiner—Edward M. Coven
Assistant Examiner—Gary Jackson
Attorney, Agent, or Firm—Robert M. Phipps

[57] ABSTRACT

Exoscopes for joining tubular like objects has a housing made in two sections which clamp around the objects to be welded together. The end of the objects are held in place by an internal stent which claps the ends of the object together. Optic fibers or the like connected to a laser source terminate in the housing in such a way that the conducted laser beam is directed simultaneously circumferentially around the abutting ends to be welded. There are no moving parts during the welding.

4 Claims, 3 Drawing Sheets

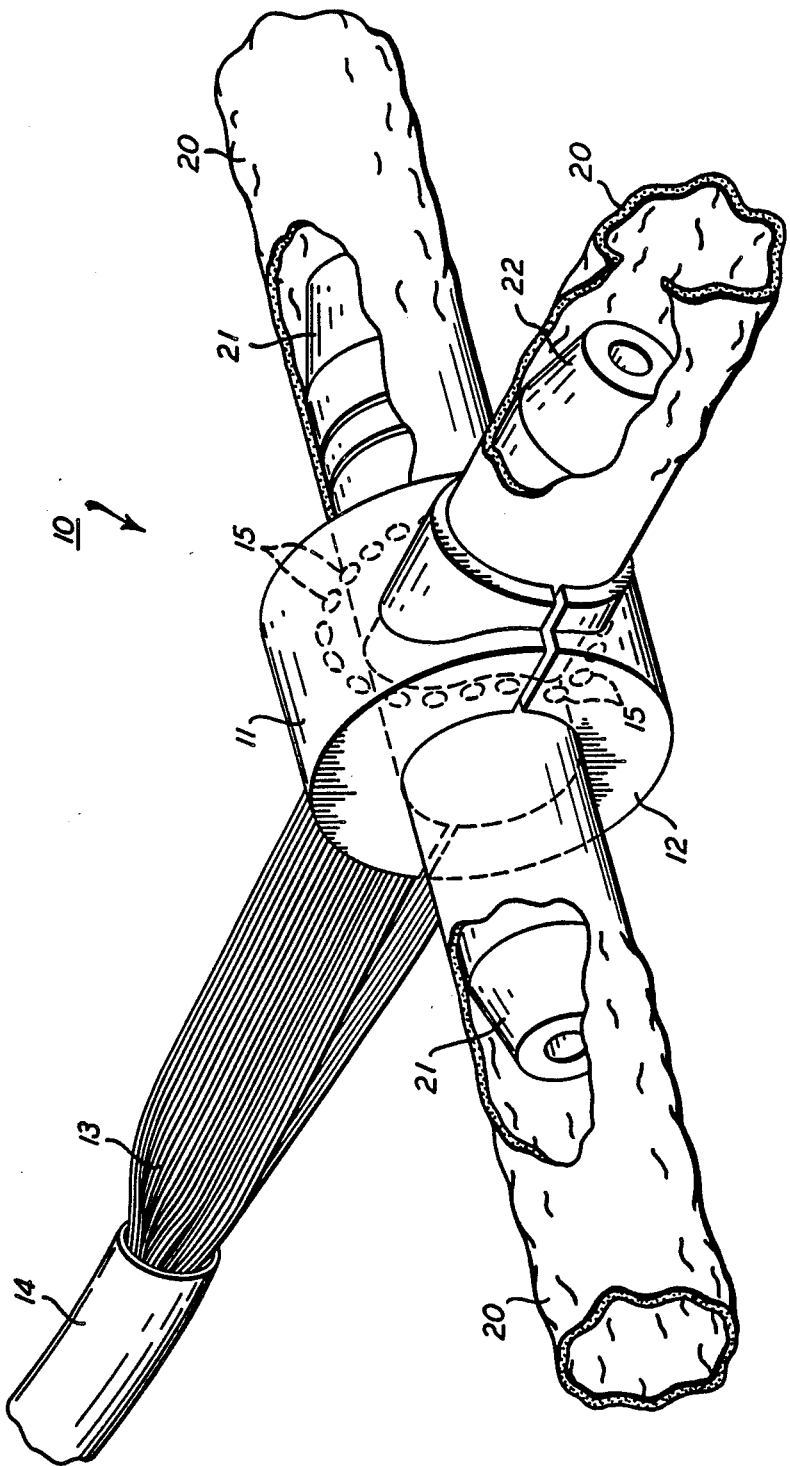

TUBULAR TISSUE WELDING DEVICE WITHOUT MOVING PARTS

RELATED APPLICATIONS

This application is a continuation in part of application Ser. No.919,954 filed Oct. 17, 1986 now abandoned and entitled "Method of Effecting Anastomosis of Tubular Tissue" which is a division of application Ser. No. 748,972 filed June 26, 1985 which is now U.S. Pat. No. 4,633,870 entitled "Apparatus for Effecting Anastomosis of Tubular Tissue".

BACKGROUND

1. Field of the Invention

This invention relates to a method and apparatus for effecting surgical anastomosis by means of laser welding. The apparatus is an exoscope which has no parts that move during welding.

2. Description of the Prior Art.

U.S. Pat. No. 4,633,870 granted on application Ser. No. 748,972 filed June 26, 1985 by Jude S. Sauer, the present applicant, discloses an exoscope, or surgical apparatus for laser welding, and a method for welding a pair of tubular tissues at their juxtaposed ends with a laser beam. The exoscope has two semi-cylindrical jaws which are releasably attachable around the abutting ends of a pair of tubular tissues that are held together by a tubular stent. A shuttle, which revolves in the jaws 360° around the outside of the junction of the tissues, is connected to a tubular conduit, that extends slidably through a handle on one of the jaws to the exterior of the instrument. The conduit contains at least three fiber-optic cords, the inner ends of which are connected to the shuttle for movement therewith, an to register with a mirror which, is also mounted on the shuttle. The outer ends of the cords are connected, respectively, to a light source for illuminating the seam which is to be welded, to a source of laser energy for directing a laser beam onto the seam, and to a lens which is utilized for observing the site where the welding is to take place.

In many instances the surgical field does not offer adequate opportunity to advantageously use the foregoing exoscope. Therefore, it is an object of this invention to provide an exoscope without moving parts, thereby avoiding the possibility of parts seizing together. An additional object is to provide exoscopes which can be of smaller size than presently possible. These and other objects will be apparent to those skilled in the art upon reference to the following detailed description.

SUMMARY OF THE INVENTION

In accordance with this invention there is provided an exoscope for joining tubular like objects comprising:

a hand-manipulable housing having first and second sections selectively movable relative to each other to form a central opening through said housing, means for releasably supporting a pair of generally cylindrically shaped sections in said central opening formed in said housing, and with confronting ends of said sections abutting each other along a seam located within said central opening, a plurality of flexible, laser light (or energy) transmissive elements extending at one end into both sections of said housing and disposed to be connected at their opposite end to a source of laser energy operable to direct a beam of laser energy through said transmissive element into said housing, means in said housing for directing said laserbeam emitted by said light transmissive element to said central opening and onto said seam, said beam directing means simultaneously directing said beam circumferentially around said central opening to all portions of said seam thereby welding together said abutting ends along said seam, said housing sections being movable away from each other at the conclusion of a welding operation, to thereby permit withdrawal of the housing from the welded cylindrical sections to disengage the later.

BRIEF DESCRIPTION OF DRAWINGS

FIG. 5 is a perspective view of an exoscope of this invention for T branched applications.

DESCRIPTION OF THE PREFERRED EMBODIMENT

Figure 1:
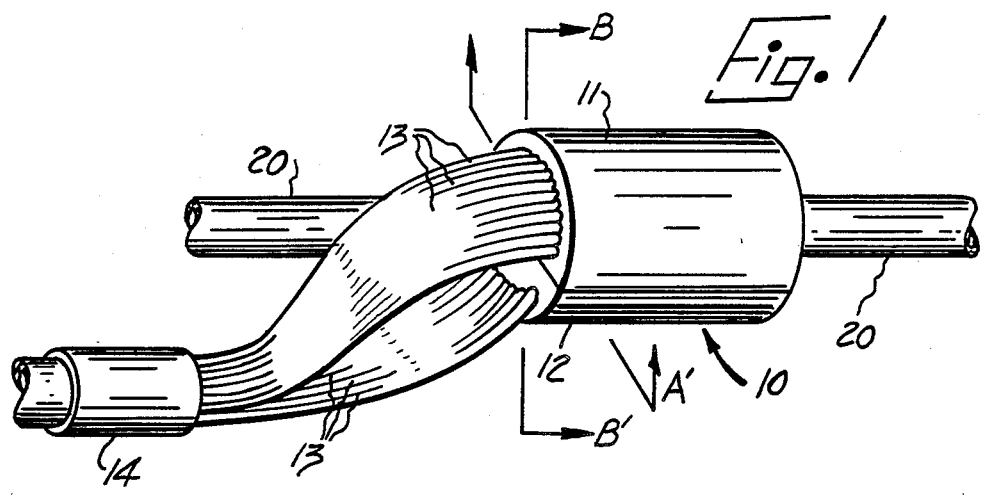
FIG. 1 is a perspective view of the exoscope according to the principles of this invention.
Figure 2:
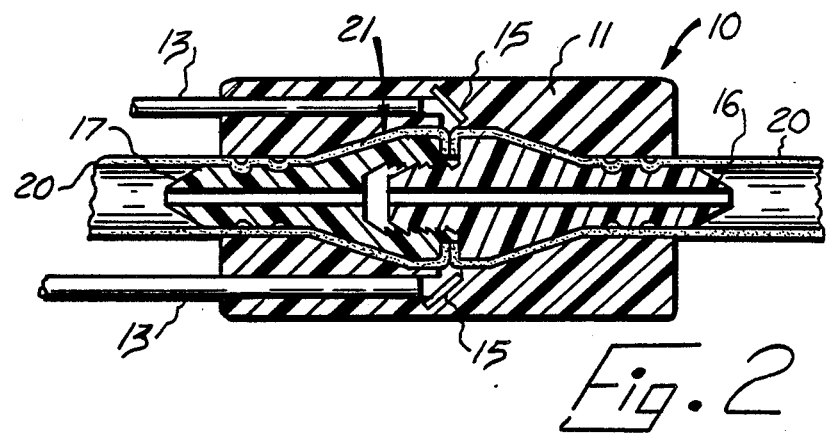
FIG. 2 is a cross section of the assembled exoscope of FIG.1 taken along line A—A'.
Figure 3:
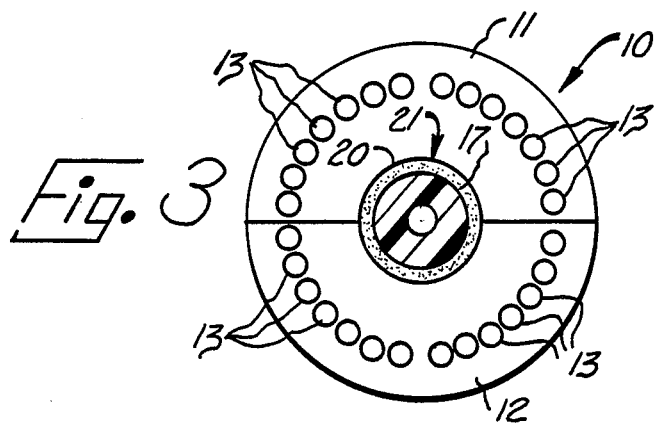
FIG. 3 is a cross sectional view of FIG. 1 taken along line B—B'.

The exterior of a preferred embodiment of this invention is shown in FIG. 1 wherein the hand-manipulable laser housing 10 is composed of a first section 11 and a second section 12 which are movable relative to each other and which when engaged together will form a central opening through the housing 10. The housing sections can be made from a variety of materials well known in the art as desired.

Flexible, light transmissive conduits or elements 13 extending at one end in both sections 11, 12 of the housing 10 and disposed to be connected at their opposite end to a source of laser energy 14 operable to direct a beam of laser energy through the conduits 13 into the housing 10. The source of laser energy or light is not shown since the mechanical aspects of obtaining laser energy is well known in the art and beyond the scope of this invention.

The housing sections 11, 12 are equipped with a laser energy beam directing means or aiming device 14. The aiming device 14 is set in a fixed position so the laser energy will always be directed to the same place. The aiming device 14 may be a flat mirror, a prism, or a concave mirror to achieve greater focusing. The degree of concave on the reflecting surface is a function of the amount of focusing desired to achieve finer, or thinner, welds. The aiming device 14 may be made from optical glass or a plastic such as polymethyl methacrylate or other polymeric compositions such as are used for the manufacture of contact lenses. The conduits 13 convey the laser energy or light from the laser energy source not shown to the aiming device 14. The aiming of the energy onto the living tissue or organ is achieved by the placement of the aiming device 14. The construction of laser energy conduit 13 can be varied depending on the particular form and source of energy desired. A particularly useful conduit material is optic fiber.

One of the uses of the exoscope of this invention is shown in the accompanying drawings. The ends of two sections of the bowel 20 are physically clamped together on the inside by use of a stent 21. The stent is comprised of two interlocking parts, one part 16 having a male coupler portion and the other part 17 having a cooperating female coupler portion. The stent 21 is sized to the approximate diameter of the organ or blood vessel 20, e.g. bowel, to be welded or fused together. The stent is more fully described in my U.S. Pat. No. 4,633,870, discussed above.

After the bowel 20 is clamped together, first one section 11 of the exoscope is placed around the clamped junction of the bowel 20 pieces. The second section 12 is then engaged with the first section 11 to complete the central opening of the housing 10. Then the surgeon exposes the bowel 20 to laser energy until separated sections of the bowel 20 are fused together. The stent can be left to dissolve in due course, or depending upon the nature of the surgery, can be removed through an opening formed in one of the other of the tubular tissues at a point axially spaced from the welded ends.

The exoscope of this invention requires no moving parts to produce a 360° circumferential laser weld of tubular tissue. Instead of having a mobile cart that carries the lasing fiber in a path around the seam, this device uses an array of multiple stationary conduits 13. This system requires a dissolvable or removable intraluminal stent 21 that circumferentially holds the ends of tubular organs 20 in apposition. It also features a housing 10 with two parts 11,12 that can be opened and closed around the stent-tissue complex. This housing 10 holds multiple conduits 13 that are positioned parallel to and completely surround the viscus to be welded. The proximal (laser) end of this optical fibers 13 are arranged in a typical round or square bundle, which can be irradiated by a single laser beam. The mistal (device) aspect of this optical cable is modified to a "spot-to-slit" conformation. Approximately half of the fiber conduits 13 go to the first section 11 of the housing 10, the remainder go to the second section 12. The distal fibers 13 of this system end just proximal to the seam to be welded. A prism or mirror 15 is positioned at a 45° angle above the entire length of the seam, so that the incoming laser light will be reflected onto the underlying abutted tissue. Thus, once this housing 10 is properly set, a single firing of the appropriate laser can produce a circumferential tissue weld.

Of course the multiple fiber conduits 13 could travel through the housing 10 perpendicular to the axis of the viscus (i.e. radially) and could overlie the seam to directly lase the abutted tissue. This would eliminate the need for a mirror 15. Because energy is lost with acute bends in optical fibers, the path of the fibers in this radial arrangement would require a larger O.D. of the housing.

From the foregoing discussion it will also be readily apparent that welds along only a part of the circumference can be obtained by directing the laser energy or light to only a selected portion of the circumference.

The exoscope is amenable to minor modifications for specific usages. A foot pedal or button for finger tip laser activation can easily be added to this system. With the provision of thermocouple (not shown) connected to a gauge (not shown) the surgeon can more accurately control the amount of laser energy applied to the tissue and insure a fusing action rather than allow the tissue to become overheated and destroyed. In a more preferred embodiment, the thermocouple is connected to a computer (also not shown) which is programed to monitor and limit, as a function of increase of temperature, the amount of laser energy applied. The computer can be additionally programed to limit available laser energy as a function of other parameters, e.g. time.

Figure 4:
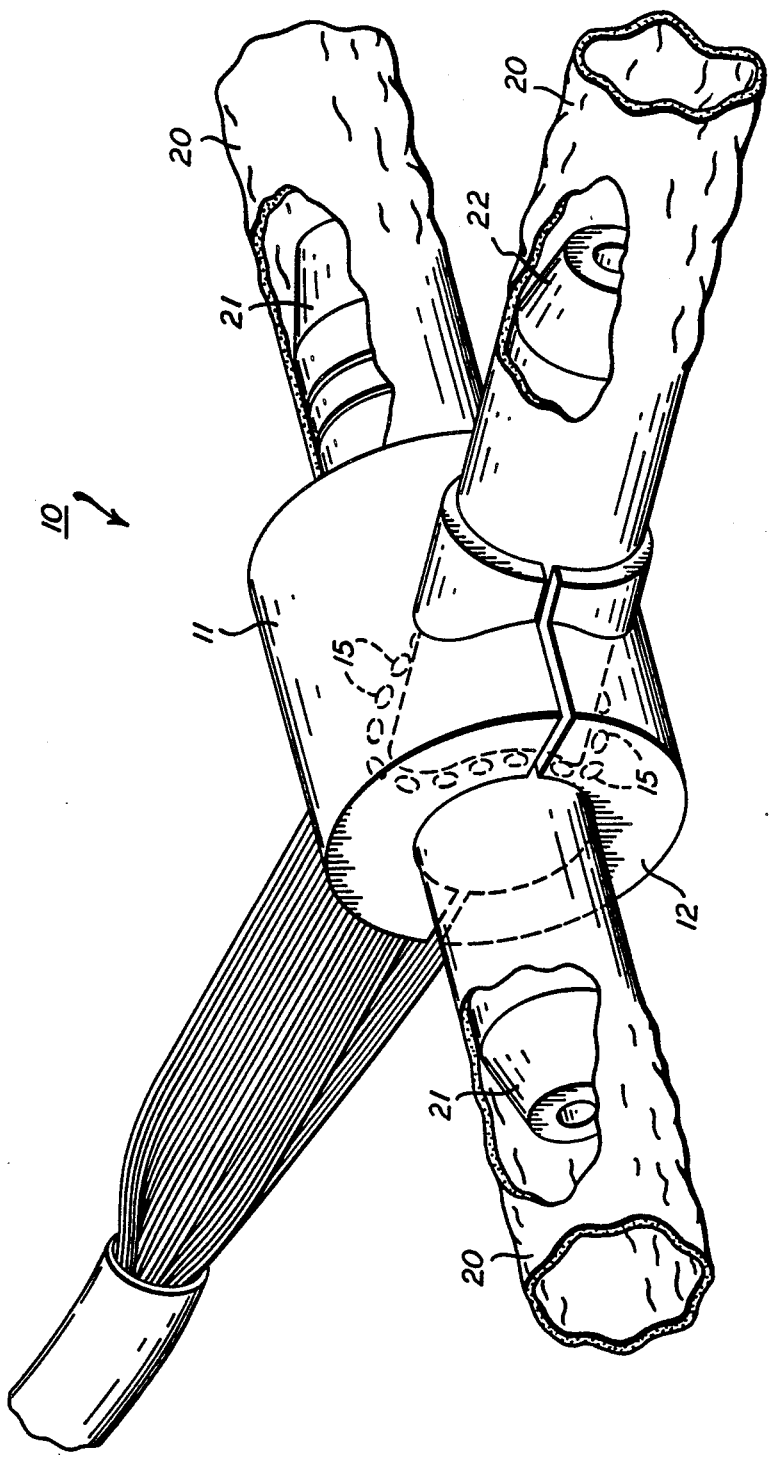
FIG. 4 is a perspective view of an exoscope of this invention for Y branched applications.

The exoscope can be configured for welding tubular material 20 in other configurations than that shown in FIG. 1. FIG. 4 illustrates a configuration which can be used when the tubular tissue 20 to be welded is in a Y branched configuration. For the Y shape the two housing members 11, 12 are modified to receive at an angle a third tube 20 with stent 22 and the aiming device 15 follows the joint line of the side branch 20. The balance of the details of this exoscope are the same as that of the exoscope of FIG. 1 above. FIG. 5 illustrates a configuration which can be used when the tubular tissue 20 to be welded is in a T branched configuration. For the T shape the two housing members 11, 12 are modified to receive at a perpendicular a third tube 20 with stent 22 and the aiming device 15 follows the joint line of the side branch 20. The balance of the details of this exoscope are the same as that of the exoscope of FIG. 1 above. In each case the branch tubular material stent 22 is fitted into stent 21.

From the foregoing it will be readily recognized that the limit on the amount or thickness of tissue, or polymeric material, to be fused is a function of the depth to which the fusing is to occur and the nature of the substrate to be fused, e.g., conductivity of laser energy and heat decomposition point.

Any laser light that is transmissible through an optical fiber or a wave guide could be used; optimal spot size, irradiance, exposure time, etc. will vary for each tissue type. There are a number of surgical devices which are capable of generating the laser beam which is applied to the laser energy conduit or fiber optic cord 13 of the illustrated embodiment. The Neodymium: Yttrium Aluminum Garnet (more commonly referred to as Neodymium: YAG or Nd:YAG) Argon-dye and copper/gold lasers can provide the laser energy for distribution by fiber optic cords. The carbon dioxide laser apparatus, which has been used in laser microsurgery is capable of producing carbon dioxide laser energy densities ranging from 50 to 750 J/cm2, the densities which have proved in the past to be suitable for the laser welding together of rabbit tissues. Low powered carbon dioxide lasers of this variety have also been used successfully in welding together severed tissues of experimental animals such as rats. This is further discussed in "Laser-assisted Vas Anastomosis, A Preliminary report" by Charles M. Lynn, MD, et al., published Lasers in Surgery and Medicine 3:261–263, 1983. However, because of the large wave length of carbon dioxide laser energy, satisfactory optic fibers 13 therefor are not yet commercially available. The exact means for generating the laser beam for use in connection with applicant's herein disclosed instruments, it will be understood, is a matter of choice and forms no part of the instant invention.

Energy control is important in the use of surgical laser tissue welding. In general, as the wavelength of the laser increases, its absorption in biological tissues becomes higher and less energy is reflected. For lasers producing visible light, the absorption coefficient is strongly dependent on the color of the tissue as well as the wavelength. For example, with the long wavelength (10.6 um) of the invisible infrared carbon dioxide laser absorption is independent of tissue color and energy is almost completely immediately absorbed by tissue water. The short wavelength (0.51 um) of the green light of the Nd: YAG laser light falls between that of carbon dioxide and argon. The Nd:YAG energy is thus absorbed by both water and tissue pigments; this absorption pattern appears best for the welding of most tissue types.

While it is known that laser energy can cause fusion of tissue, the complete process that produces a tissue weld is not fully understood. It is well accepted that tissue collagen provides for the vast majority of the strength of most tissues. In earlier work with rabbit bowel, using collagen specific tissue stain and light microscopy, it was shown there was a clear alteration of collagen at the tissue weld sites. In a recent report in *Science*, the mechanism of tissue welding was further explored. These authors maintained that laser induced alterations of the collagen substructure allows for microsurgical tissue welding via a heat induced homogenization change in collagen with interdigitalization of the altered individual collagen fibrils. In other words, as clearly seen in their electron microscopy slides, the usually well organized tissue collagen becomes unraveled during tissue welding. During tissue cooling, this unraveled collagen appears to become tangled in adjacent unraveled collagen to produce tissue bonds. Direct radiant effects from the laser light may also provide some small component of weld strength by a yet undescribed effect on other tissue proteins. Thus, most investigators agree that tissue welding is primarily produced by a thermal induced fusion of tissue collagen; the most effective welding temperature is presently believed to be approximately 62° C.

The exoscope of this invention is also useful for welding many other types of tissue (e.g. blood vessels—for hemostasis or anastomoses, etc.). Also, the exoscope can be used to fuse plastic, e.g., polyfluoroethylene or a polyimide, to human tissue as in the replacement of veins or arteries. Thus, the tissue can be a polymeric material which is a living organism or a non living polymer which is typical in the shape of sheeted material.

Outside a living body the exoscope can be used to fuse two or more tubes made from the above plastics when delicate, precise welding is required.

Because there are no moving parts, this exoscope device has the following advantages:

1. No moving parts to jam or malfunction.
2. It can be smaller. The size of an exoscope is limited by the required diameter of the cart track. This device could potentially have a diameter of several millimeters.
3. Can easily be made and used as a disposable device.
4. Arrangement of lasing path is unlimited. In addition to end-to-end anastomoses as described, end-to-side (T or Y configurations) and fish-mouth patterns are some examples of where a side branch tube is attached to the main tube.
5. Entire seam can be irradiated at once. Duration of lasing mandated by tissue requirements, not by time it takes for cart to travel.
6. Many fiber conduits 13 could be employed to make small spot sizes.

The foregoing examples and methods have been described in the foregoing specification for the purpose of illustration and not limitation. Many modifications and ramifications will naturally suggest themselves to those skilled in the art based on this disclosure. These are intended to be comprehended as within the scope of this invention.

The embodiments of the invention in which as exclusive property or privilege is claimed are defined as follows:

1. An exoscope for joining tubular like objects comprising:
    a hand-manipulable housing having first and second sections selectively movable relative to each other to form an unitary housing with a central opening lengthwise through said housing,
    means for releasably supporting a pair of generally cylindrically shaped sections in said central opening formed in said housing, and with confronting ends of sections abutting each other along a seam located within said central opening,
    a plurality of flexible, light transmissive elements extending at one into fixed sites in both sections of said housing and disposed to be connected at their opposite end to a source of laser energy operable to direct a beam of laser energy through said transmissive element into said housing,
    means in said housing for directing said laser beam emitted from said light transmissive element to said central opening and onto said seam, said beam directing means simultaneously directing said beam circumferentially around said central opening to all portions of said seam thereby welding together said abutting ends along said seam, said housing sections being movable away from each other at the conclusion of a welding operation, to thereby permit withdrawal of the housing from the welded cylindrical sections to disengage the later said two housing sections being all of the housing sections required for joining tubular like objects.

2. The exoscope of claim 1 wherein the central housing forms a cylindrical opening.

3. The exoscope of claim 1 wherein the central housing forms a Y-shaped tubular opening.

4. The exoscope of claim 1 wherein the central housing forms a T-shaped tubular opening.

* * * * *